Aug. 12, 1947. O. H. HEIDER Plant Pat. 751
APRICOT TREE
Filed Sept. 9, 1946
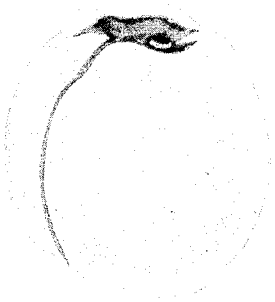
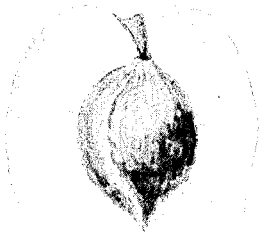
INVENTOR
Otto H. Heider
By Orville M. Kile
PLANT PATENT AGENT Patented Aug. 12, 1947

Plant Pat. 751

UNITED STATES PATENT OFFICE

751

APRICOT TREE

Otto H. Heider, Entiat, Wash., assignor to Columbia & Okanogan Nursery Company, Wenatchee, Wash.

Application September 9, 1946, Serial No. 695,582

1 Claim. (Cl. 47—62)

My present discovery relates to a new and improved variety of apricot tree, the qualities of the fruit being outstanding for commercial purposes. It ripens early and produces highly colored and sweet-flavored fruit with firm flesh, thus making an excellent shipping and canning fruit in an early season.

My new variety is a seedling which is presumably a cross between Wenatchee Moorpark and an unknown variety. Some years ago I planted about six seeds of the Wentachee Moorpark in my yard. These all came up but since they had been planted too close together, I grubbed out all but one of the seedlings which seemed most promising and which resulted in the present new variety. It has since been reproduced by budding done by a nurseryman, and the fruit of the budded trees is identical in every respect to that on the original tree of this new variety from which the buds were taken.

The accompanying illustration shows one of the fruits and a cross-section of another fruit of this variety in approximately their true colors when fully tree ripened. These are typical fruits but allowance must be made for slight variations between specimens.

There is no appreciable difference between the tree and foliage of my new variety and that of Wenatchee Moorpark. In fact, they appear to be identical. Following is a detailed description of the fruit of my new variety, color plate references being to Ridgway's Color Standards and Nomenclature.

Shape: Somewhat elongated and blocky. Sides compressed so as to make the fruit's transverse cross section elliptical. Shoulders and surface irregular when fruit ripens.

Cavity: Regular in form and medium in depth.

Suture: Medium to shallow.

Size: Larger than most popular varieties, including Wenatchee Moorpark as well as the subject of Plant Patent No. 74. It measures approximately 2 inches in its largest transverse diameter and 2¼ inches in vertical diameter.

Skin: Piquant in flavor. Smooth with high gloss. Very highly colored, fully tree-ripened fruit being between Orange Chrome and Flame Scarlet (Plate II).

Flesh: Exceptionally firm and fine in texture with little fiber. Juicy when ripe. Flavor sweet. Color very dark—about same as skin.

Maturity: Ripens about a week to ten days earlier than Wenatchee Moorpark; about with the subjects of Plant Patents 74 and 630.

Ripening habit: Ripens slowly. Colors very evenly while still hard ripe, thus making it possible to pick and ship while in prime condition.

Stone: Smaller than that of Wenatchee Moorpark, measuring approximately 1¼ inches by slightly less than one inch, allowing a larger proportion of flesh. Entirely free from the flesh when ripe. Light brown in color.

*Comparison*

The variety known to me which is most nearly like my new variety is the Wenatchee Moorpark, but the two varieties differ principally in the following respects.

1. My new variety ripens 7 to 10 days earlier.
2. Shape of the fruit of my variety is long and blocky while that of the Wenatchee Moorpark is more globular.
3. My variety produces fruit which is consistently larger.
4. The fruit of my new variety is firmer in texture.
5. The stone of my fruit is smaller.
6. The fruit of my variety ripens more evenly. Wenatchee usually colors on one side while the other side is green, but my new variety colors evenly while still hard ripe.
7. Fruit of my new variety has smoother, glossier skin, it being very wax-like.
8. The fruit of my new variety is a darker, richer color both of skin and of flesh.

Having thus disclosed my discovery, I claim:

The new and useful variety of apricot tree, substantially as herein shown and described, characterized particularly by its early ripening date and its large, somewhat elongated fruit having glossy dark rich-colored skin, small stone, firm, sweet-flavored, fine-textured, dark flesh which is juicy when ripe, and the quality of ripening and coloring evenly while still hard ripe.

OTTO H. HEIDER.